US012642461B2

(12) United States Patent
Tajiri

(10) Patent No.: US 12,642,461 B2
(45) Date of Patent: Jun. 2, 2026

(54) DETECTING DEVICE AND MEASURING APPARATUS

(71) Applicant: SEIKO EPSON CORPORATION, Tokyo (JP)

(72) Inventor: Takashi Tajiri, Matsumoto (JP)

(73) Assignee: SEIKO EPSON CORPORATION, Tokyo (JP)

( * ) Notice: Subject to any disclaimer, the term of this patent is extended or adjusted under 35 U.S.C. 154(b) by 880 days.

(21) Appl. No.: 17/975,612

(22) Filed: Oct. 28, 2022

(65) Prior Publication Data

US 2023/0132704 A1 May 4, 2023

(30) Foreign Application Priority Data

Oct. 29, 2021 (JP) .................................. 2021-177279

(51) Int. Cl.
| | |
|---|---|
| *A61B 5/1455* | (2006.01) |
| *A61B 5/0205* | (2006.01) |
| *A61B 5/024* | (2006.01) |
| *A61B 5/00* | (2006.01) |

(52) U.S. Cl.
CPC ........ *A61B 5/14552* (2013.01); *A61B 5/0205* (2013.01); *A61B 5/024* (2013.01); *A61B 5/681* (2013.01); *A61B 2562/04* (2013.01)

(58) Field of Classification Search
CPC .............. A61B 5/1455; A61B 5/14552; A61B 5/02416; A61B 5/681
See application file for complete search history.

(56) References Cited

U.S. PATENT DOCUMENTS

| | | | | |
|---|---|---|---|---|
| 8,275,432 | B2 * | 9/2012 | Kuhn ................. | A61B 5/14552 |
| | | | | 600/323 |
| 9,439,569 | B2 | 9/2016 | Shimuta | |
| 9,814,399 | B2 * | 11/2017 | Takahashi .......... | A61B 5/02416 |
| 10,111,592 | B2 | 10/2018 | Shimuta | |
| 10,219,709 | B2 * | 3/2019 | Basu ................... | A61B 5/14552 |
| 10,314,526 | B2 * | 6/2019 | Shimuta ............. | A61B 5/14552 |
| 11,185,243 | B2 | 11/2021 | Böscke et al. | |
| 2001/0056243 | A1 | 12/2001 | Ohsaki et al. | |
| 2014/0151586 | A1 | 6/2014 | Shimuta | |

(Continued)

FOREIGN PATENT DOCUMENTS

| | | |
|---|---|---|
| CN | 103732135 | 4/2014 |
| JP | 2001353133 | 12/2001 |
| JP | 2012254194 | 12/2012 |

(Continued)

*Primary Examiner* — Eric F Winakur
(74) *Attorney, Agent, or Firm* — JCIPRNET

(57) ABSTRACT

The detecting device according to the present disclosure includes a light-emitting portion emitting light, a light-receiving portion receiving the light emitted from the light-emitting portion and exiting from a living body, a holding member holding the light-emitting portion and the light-receiving portion, a sealing member sealing the light-emitting portion and the light-receiving portion, a cover member covering the holding member sealed by the sealing member, and a light transmissive member interposed between the sealing member and the cover member, wherein n1≤n2≤n3, where n1 is a refractive index of the sealing member, n2 is a refractive index of the light transmissive member, and n3 is a refractive index of the cover member.

3 Claims, 5 Drawing Sheets

(56)          References Cited

U.S. PATENT DOCUMENTS

| | | |
|---|---|---|
| 2016/0235310 A1 | 8/2016 | Shimuta |
| 2019/0223738 A1 | 7/2019 | Böscke et al. |

FOREIGN PATENT DOCUMENTS

| | | |
|---|---|---|
| JP | 2019519272 | 7/2019 |
| JP | 2019166267 | 10/2019 |
| JP | 2020202976 | 12/2020 |
| WO | 2013027357 | 2/2013 |

* cited by examiner $n1 < n2 < n3$

DETECTING DEVICE AND MEASURING APPARATUS

The present application is based on, and claims priority from JP Application Serial Number 2021-177279, filed Oct. 29, 2021, the disclosure of which is hereby incorporated by reference herein in its entirety.

BACKGROUND

1. Technical Field

The present disclosure relates to a detecting device and a measuring apparatus.

2. Related Art

Various measurement techniques for non-invasively measuring biological information such as pulse waves have been proposed. For example, JP-A-2001-353133 discloses, regarding a detecting device including a light-emitting portion allowing light to exit to a living body and a light-receiving portion receiving the light that exits from the light-emitting portion, is reflected by the living body, and thus is incident on the light-receiving portion, a technique for enhancing intimate contact between the living body and a cover covering the light-emitting portion and the light-receiving portion.

However, the above detecting device has a problem in that light from the light-emitting portion reflected by the back surface of the cover member is incident on the light-receiving portion as stray light, thereby decreasing detection accuracy.

SUMMARY

According to an aspect of the present disclosure, provided is a detecting device including a light-emitting unit that emits a light, a light-receiving unit that receives the light emitted from the light-emitting unit and exiting from a living body, a holding member that holds the light-emitting unit and the light-receiving unit, a sealing member that covers the light-emitting unit and the light-receiving unit, a cover member that covers the holding member sealed by the sealing member, and a light transmissive member that is between the sealing member and the cover member, wherein n1≤n2≤n3 where n1 is a refractive index of the sealing member, n2 is a refractive index of the light transmissive member, and n3 is a refractive index of the cover member.

According to an aspect of the present disclosure, provided is a detecting device including a light-emitting unit emitting light to a living body, a light-receiving unit receiving the light from the living body, a holding member holding the light-emitting unit and the light-receiving unit, a wall member for light shielding disposed, at the holding member, between the light-emitting unit and the light-receiving unit, a sealing member sealing the light-emitting unit and the light-receiving unit, a cover member covering the holding member sealed by the sealing member, and a light transmissive member interposed between the sealing member and the cover member, wherein the wall member is formed to divide the sealing member into an accommodation space for the light-emitting unit and an accommodation space for the light-receiving unit and to reach the light transmissive member from a bottom surface of the holding member, and a refractive index value of the light transmissive member is equal to or less than a refractive index value of the cover member.

According to an aspect of the present disclosure, provided is a measuring apparatus including the detecting device according to the above aspect, and an information analysis portion determining biological information from a detection signal indicating a detection result from the detecting device.

DESCRIPTION OF EXEMPLARY EMBODIMENTS

Embodiments of the present disclosure will be described below with reference to the accompanying drawings. Note that, to illustrate each member in a recognizable size in the following drawings, the scale and the angle of each member are different from an actual scale and an actual angle.

First Embodiment

Figure 1:
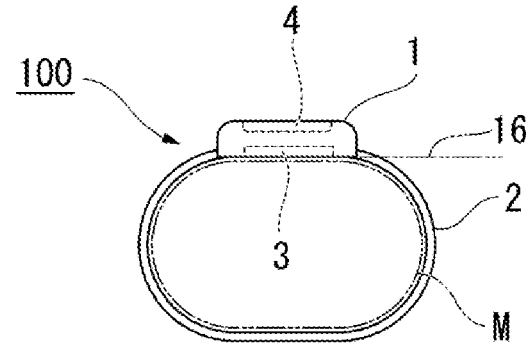
FIG. 1 is a side view of a measuring apparatus according to a first embodiment.

FIG. 1 is a side view of a measuring apparatus 100 according to a first embodiment. The measuring apparatus 100 according to the first embodiment illustrated in FIG. 1 is a biometer non-invasively measuring biological information of a subject (e.g., human), which is an example of a living body, and is mounted at a measurement target site (hereinafter referred to as "measurement site") M of the body of the subject. The measuring apparatus 100 according to the first embodiment is a wristwatch-type portable device including a main body 1 and a belt 2 and can be worn around a wrist, which is an example of the measurement site (living body) M, of the subject by winding the belt 2 having a band shape around the wrist. In the first embodiment, examples of the biological information include a pulse wave (e.g., pulse rate) and oxygen saturation (SpO2) of the subject. The pulse wave means a time change in volume within a blood vessel associated with a beat of the heart. The oxygen saturation means a percentage (%) of hemoglobin combined with oxygen in hemoglobin in blood of the subject and is an index for evaluating a respiratory function of the subject.

Figure 2:
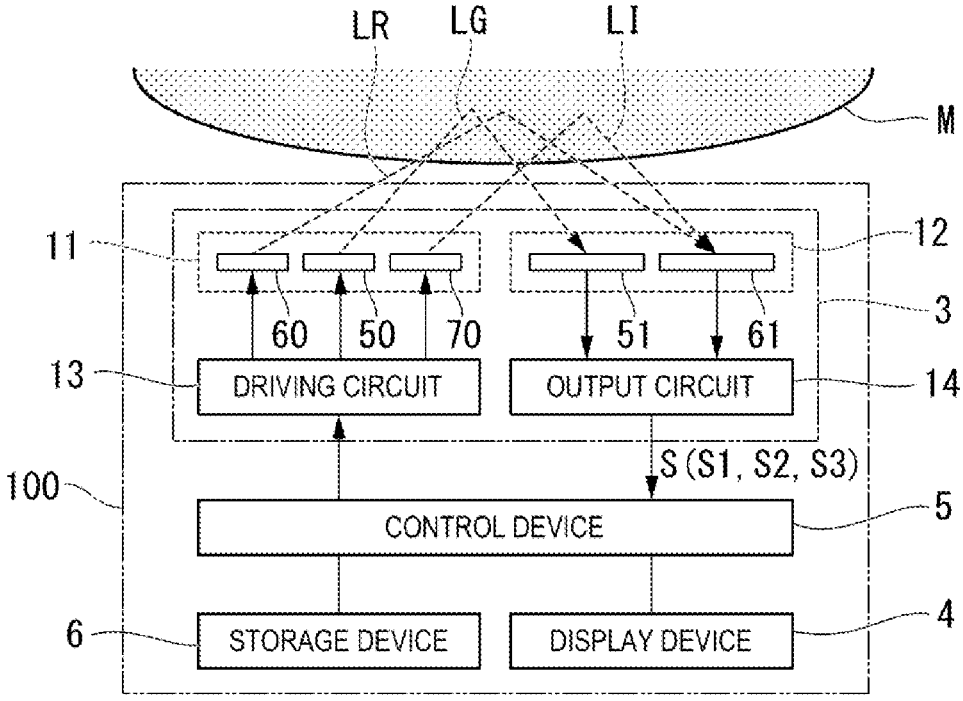
FIG. 2 is a configuration diagram focusing on a function of the measuring apparatus.

FIG. 2 is a configuration diagram focusing on a function of the measuring apparatus 100. As illustrated in FIG. 2, the measuring apparatus 100 according to the first embodiment includes a control device 5, a storage device 6, a display device 4, and a detecting device 3. The control device 5 and the storage device 6 are installed inside the main body 1. As illustrated in FIG. 1, in the main body 1, the display device 4 is installed at a surface on the opposite side of the measurement site M, and displays various images including measurement results under control by the control device 5. The display device 4 is, for example, a liquid crystal display panel.

The detecting device 3 is an optical sensor module generating a detection signal S according to the state of the measurement site M. As illustrated in FIG. 1, the detecting device 3 is installed in the main body 1, for example, at a surface (hereinafter referred to as a detection surface) 16 facing the measurement site M. The detection surface 16 is a surface in contact with the measurement site M. As illustrated in FIG. 2, the detecting device 3 according to the first embodiment includes a light-emitting unit portion (light-emitting portion) 11, a light-receiving unit portion (light-receiving portion) 12, a driving circuit 13, and an output circuit 14. Note that one or both of the driving circuit 13 and the output circuit 14 can be installed as external circuits of the detecting device 3. That is, the driving circuit 13 and the output circuit 14 can be omitted from the detecting device 3.

The light-emitting unit portion 11 includes a first light-emitting element 50, a second light-emitting element 60, and a third light-emitting element 70. The first light-emitting element 50, the second light-emitting element 60, and the third light-emitting element 70 are elements emitting light having different wavelengths to the measurement site M.

The first light-emitting element 50 allows green light (first light) LG having a green wavelength range from 520 nm to 550 nm to exit to the measurement site M. The green light LG according to the first embodiment is, for example, light having a peak wavelength of 520 nm.

The second light-emitting element 60 allows red light (second light) LR having a red wavelength range, for example, from 600 nm to 800 nm to exit to the measurement site M. The red light LR according to the first embodiment is, for example, light having a peak wavelength of 660 nm.

The third light-emitting element 70 allows near-infrared light (third light) LI having a near-infrared wavelength range, for example, from 800 nm to 1300 nm to exit to the measurement site M. The near-infrared light LI according to the first embodiment is, for example, light having a peak wavelength of 905 nm.

As light-emitting elements constituting the first light-emitting element 50, the second light-emitting element 60, and the third light-emitting element 70, for example, bare chip light-emitting diodes (LEDs) or bullet-shaped LEDs are preferably used. Note that the wavelength of the light exiting from each of the light-emitting portions is not limited to the numerical ranges described above. Hereinafter, when the first light-emitting element 50, the second light-emitting element 60, and the third light-emitting element 70 are not particularly distinguished, these elements are collectively referred to as the respective light-emitting elements 50, 60, and 70.

The driving circuit 13 allows the respective light-emitting elements 50, 60, and 70 to emit light by supplying drive currents. The driving circuit 13 according to the first embodiment allows the respective light-emitting elements 50, 60, and 70 to periodically emit light in a time-division manner. The light exiting from the respective light-emitting elements 50, 60, and 70 is incident on the measurement site M and propagates in the measurement site M while being repeatedly reflected and scattered. Then, the light exits toward the main body 1 and reaches the light-receiving unit portion 12. That is, the detecting device 3 according to the first embodiment is a reflective optical sensor in which the light-emitting unit portion 11 and the light-receiving unit portion 12 are located on one side relative to the measurement site M.

The light-receiving unit portion 12 receives the light coming from the measurement site M by light emission of the light-emitting unit portion 11. The light-receiving unit portion 12 according to the first embodiment includes a first light-receiving element 51 and a second light-receiving element 61. The first light-receiving element 51 and the second light-receiving element 61 each generate a detection signal corresponding to the intensity of the received light. Hereinafter, when the first light-receiving element 51 and the second light-receiving element 61 are not particularly distinguished, these elements are collectively referred to as "respective light-receiving elements 51 and 61".

The first light-receiving element 51 receives the green light LG exiting from the light-emitting element 50 and propagating inside the measurement site M and generates a detection signal corresponding to the intensity of the received light. The second light-receiving element 61 receives the red light LR exiting from the second light-emitting element 60 and propagating inside the measurement site M or the near-infrared light LI exiting from the third light-emitting element 70 and propagating inside the measurement site M, and generates a detection signal corresponding to the intensity of the received light.

The output circuit 14 includes, for example, a A/D converter converting the detection signal generated by each of the light-receiving elements 51 and 61 from analog to digital, and an amplifier circuit amplifying the detection signal after the conversion (both are omitted in the figure), and generates a plurality of detection signals S (S1, S2, S3) corresponding to the mutually different wavelengths.

The detection signal S1 is a signal representing the intensity of the light received by the first light-receiving element 51 when the green light LG exiting from the light-emitting element 50 is received. The detection signal S2 is a signal representing the intensity of the light received by the second light-receiving element 61 when the red light LR exiting from the second light-emitting element 60 is received. The detection signal S3 is a signal representing the intensity of the light received by the second light-receiving element 61 when the near-infrared light LI exiting from the third light-emitting element 70 is received.

The amount of light absorbed by blood is usually different between when the blood vessel is dilated and constricted, and thus each detection signal S is a pulse wave signal including a periodically fluctuating component corresponding to a pulsating component (volume pulse wave) of the artery inside the measurement site M.

Note that the driving circuit 13 and the output circuit 14 are mounted, in the form of an IC chip, at a wiring substrate, together with the light-emitting unit portion 11 and the light-receiving unit portion 12. Note that, as described above, the driving circuit 13 and the output circuit 14 can be installed outside the detecting device 3.

The control device 5 is an arithmetic processing device such as a central processing unit (CPU) or a field-programmable gate array (FPGA), and controls the entire measuring apparatus 100. The storage device 6 includes, for example, a non-volatile semiconductor memory, and stores a program executed by the control device 5 and various data used by the control device 5. Note that a configuration in which functions of the control device 5 are distributed to a plurality of integrated circuits, or a configuration in which some or all functions of the control device 5 are implemented by dedicated electronic circuits can be employed. Note that, while the control device 5 and the storage device 6 are illustrated as separate elements in FIG. 2, the control device 5 including the storage device 6 therein can be implemented by, for example, an application specific integrated circuit (ASIC).

The control device 5 according to the first embodiment executes the program stored in the storage device 6 to determine biological information of the subject from the plurality of detection signals S (S1, S2, S3) generated by the detecting device 3. Specifically, the control device 5 can determine the pulse interval (PPI) of the subject from the detection signal S1 representing the intensity of the green light LG received by the first light-receiving element 51. Additionally, the control device 5 can determine the oxygen saturation (SpO2) of the subject by analyzing the detection signal S2 representing the intensity of the red light LR received by the second light-receiving element 61 and the detection signal S3 representing the intensity of the near-infrared light LI received by the second light-receiving element 61.

As described above, in the measuring apparatus 100 according to the first embodiment, the control device 5 functions as an information analysis portion for determining the biological information from the detection signals S indicating the detection results by the detecting device 3. The control device (the information analysis portion) 5 displays, on the display device 4, the biological information determined from the detection signals S. Note that a user can be notified of the measurement results by voice output. A configuration is also preferable in which a user is notified of a warning (possibility of a physical dysfunction) when the pulse rate or the oxygen saturation varies to a numerical value outside a predetermined range.

Figure 3:
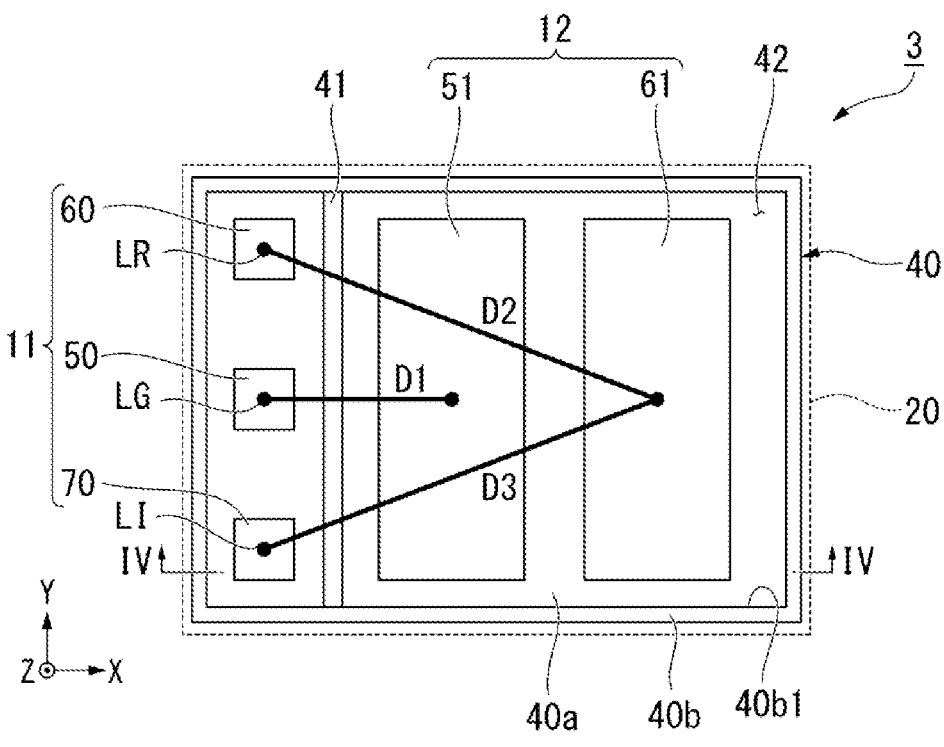
FIG. 3 is a plan view of a detecting device.
Figure 4:
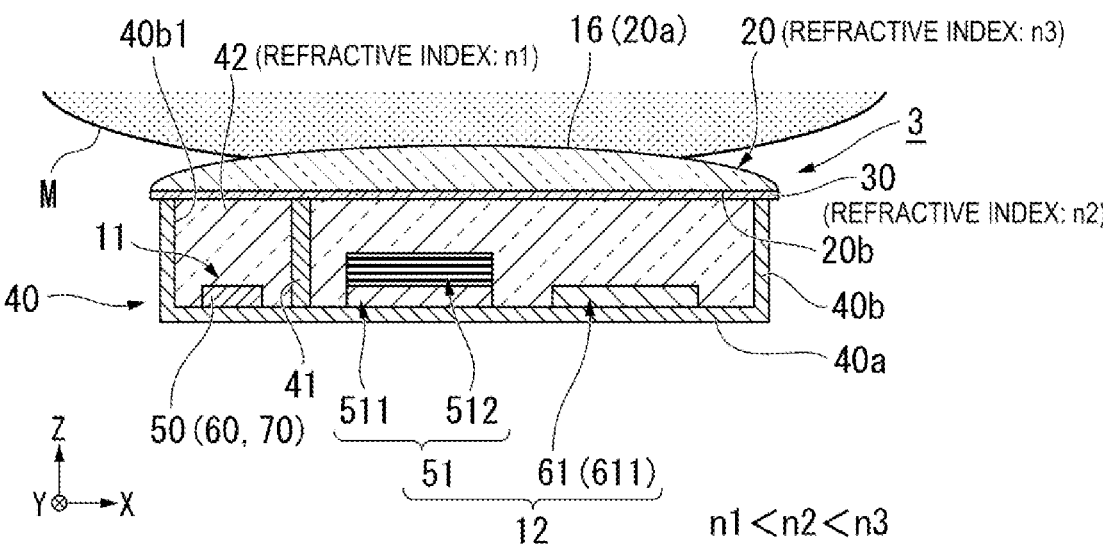
FIG. 4 is a cross-sectional view taken along line IV-IV in FIG. 3.

FIG. 3 is a plan view of the detecting device 3 according to the first embodiment. FIG. 4 is a cross-sectional view taken along line IV-IV in FIG. 3. As illustrated in FIGS. 3 and 4, the detecting device 3 according to the first embodiment further includes, in addition to the light-emitting unit portion 11 and the light-receiving unit portion 12, a cover member 20, an intermediate member (light transmissive member) 30, a housing 40, and a sealing member 42. Note that the driving circuit 13 and the output circuit 14 are omitted in FIGS. 3 and 4.

The configuration of the detecting device 3 will be described below using an XYZ coordinate system. The X-axis corresponds to an axis along a long side (one side) of the housing 40 having a rectangular outer shape. The Y-axis corresponds to an axis that is orthogonal to the X-axis and is along a short side (another side) of the housing 40. The Z-axis corresponds to an axis that is orthogonal to the X-axis and Y-axis and is along a thickness direction of the housing 40.

As illustrated in FIGS. 3 and 4, the housing 40 is a member holding the elements (the light-emitting unit portion 11 and the light-receiving unit portion 12) constituting the detecting device 3. The housing 40 has a box shape and includes a bottom surface portion 40a having a rectangular flat-plate shape, a wall portion 40b having a rectangular frame shape and protruding from the peripheral edge of the bottom surface portion 40a toward the +Z-side, and a wall portion 41 for light shielding. The housing 40 is formed of, for example, aluminum. An inner peripheral surface 40b1 of the wall portion 40b is colored black and thus has a light-shielding property. This suppresses reflection by the inner peripheral surface 40b1 of the wall portion 40b.

Note that the material and the manufacturing method of the housing 40 are freely determined. For example, the housing 40 can be formed by injection molding of a resin material. A configuration in which the housing 40 is formed integrally with the main body 1 is also preferable.

The light-emitting unit portion 11 and the light-receiving unit portion 12 are installed on the bottom surface portion 40a of the housing 40 while being mounted on a wiring substrate (not illustrated).

The wall portion 41 for light shielding is disposed between the light-emitting unit portion 11 and the light-receiving unit portion 12 in a direction along the X-axis. The wall portion 41 for light shielding is a plate member protruding from the bottom surface portion 40a toward the +Z side and extending in the Y-axis direction, and divides the accommodation space in the housing 40 into two in the X-axis direction. That is, the wall portion 41 for light shielding separates the space accommodating the light-emitting unit portion 11 and the light-receiving unit portion 12 in the direction along the X-axis. The wall portion 41 for light shielding is a wall shielding light so that light exiting from the light-emitting unit portion 11 is not directly incident on the light-receiving unit portion 12. It is also possible to say that the wall portion 41 for light shielding is a member partially shielding the green light LG, the red light LR, and the near-infrared light LI. In the example illustrated in FIG. 4, the wall portion 41 for light shielding is formed to divide the sealing member 42 into the accommodation space for the light-emitting unit portion 11 and in the accommodation space for the light-receiving unit portion 12 and to reach the intermediate member 30 from the bottom surface portion 40a of the housing 40. In the case of the first embodiment, as described below, the refractive index value of the intermediate member 30 is equal to or less than the refractive index value of the cover member 20.

The sealing member 42 is a transparent material sealing (molding to) the light-emitting unit portion 11 and the light-receiving unit portion 12. As the material of the sealing member 42, for example, a UV-curable or ultraviolet-curable optical adhesive that is transmissive is used. The refractive indexes of these optical adhesives are, for example, approximately from 1.3 to 1.5.

A gap between the light-emitting unit portion 11 and the light-receiving unit portion 12 accommodated in the housing 40 and the wall portion 40b is filled with the sealing member 42. In the first embodiment, the sealing member 42 seals the light-emitting elements 50, 60, and 70 and the light-receiving elements 51 and 61. In the first embodiment, the upper surface of the sealing member 42 is flush with the upper surface of the wall portions 40b and 41 of the housing 40.

The cover member 20 covers the housing 40 sealed by the sealing member 42. The cover member 20 is composed of, for example, a light transmissive member. As the material of the cover member 20, for example, acrylic (refractive index: 1.49) or polycarbonate (refractive index: 1.585) is used.

In the first embodiment, the cover member 20 includes a convex portion 20a. The convex portion 20a is a curved surface protruding toward the measurement site M and functions as the detection surface 16. In the cover member 20, the surface 20b on the opposite side of the convex portion 20a is configured as a flat surface. The cover member 20 according to the first embodiment is a plano-convex cover having one surface configured as a curved surface and another surface configured as a flat surface. The cover member 20 according to the first embodiment includes the detection surface 16 including the convex portion 20a, thereby allowing the detection surface 16 and the measurement site M to favorably contact each other. This can suppress the intrusion of stray light components from the gap between the detection surface 16 and the measurement site M.

The intermediate member 30 is a light transmissive member interposed between the sealing member 42 and the cover member 20. Similar to the sealing member 42, an optical adhesive having, for example, a refractive index of approximately 1.3 to 1.5 is used as the material of the intermediate member 30. In the first embodiment, the intermediate member 30 functions as a joint material joining the cover member 20 to the sealing member 42 and the housing 40.

The constituent materials of the sealing member 42 and the intermediate member 30 are appropriately selected so as to satisfy the condition that the refractive index n1 of the sealing member 42 is smaller than the refractive index n2 of the intermediate member 30.

The constituent materials of the intermediate member 30 and the cover member 20 are also appropriately selected so as to satisfy the condition that the refractive index n2 of the intermediate member 30 is smaller than the refractive index n3 of the cover member 20.

In the first embodiment, the refractive indexes of the sealing member 42, the intermediate member 30, and the cover member 20 satisfy the relationship of n1<n2<n3.

Note that the refractive index difference between the refractive index n1 of the sealing member 42 and the refractive index n2 of the intermediate member 30 is desirably as small as possible. The refractive index difference between the refractive index n2 of the intermediate member 30 and the refractive index n3 of the cover member 20 is desirably as small as possible.

The light-emitting unit portion 11 is installed in the housing 40 such that the light-emitting surfaces of the respective light-emitting elements 50, 60 and 70 are parallel to the XY plane. That is, the respective light-emitting elements 50, 60, and 70 emit light toward the +Z-side.

The light-receiving unit portion 12 is installed in the housing 40 such that the light-receiving surfaces of the respective light-receiving elements 51 and 61 are parallel to the XY plane. That is, the respective light-receiving elements 51 and 61 receive light incident from the Z direction.

As illustrated in FIG. 3, the light-emitting elements 50, 60, and 70 are arranged side by side at intervals in a direction along the Y-axis (first direction). Specifically, the second light-emitting element 60 is disposed on the +Y side of the first light-emitting element 50, and the third light-emitting element 70 is disposed on the −Y side of the first light-emitting element 50. That is, the first light-emitting element 50 is disposed between the second light-emitting element 60 and the third light-emitting element 70 in the direction along the Y-axis. It can be also said that the first light-emitting element 50 is located between the second light-emitting element 60 and the third light-emitting element 70.

The light-receiving elements 51 and 61 are arranged side by side at intervals in a direction along the X-axis (second direction) intersecting (orthogonal to) the Y-axis. Specifically, the first light-receiving element 51 is disposed on the +X side of the light-emitting unit portion 11, and the second light-receiving element 61 is disposed on the +X side of the first light-receiving element 51. That is, the second light-receiving element 61 is disposed on the opposite side of the light-emitting unit portion 11 with respect to the first light-receiving element 51.

Here, the distance from the first light-emitting element 50 to the first light-receiving element 51 is denoted as D1, the distance from the second light-emitting element 60 to the second light-receiving element 61 is denoted as D2, and the distance from the third light-emitting element 70 to the second light-receiving element 61 is denoted as D3. The distance D1 corresponds to the distance between the centers of the first light-emitting element 50 and the first light-receiving element 51 in plan view from the Z-axis direction. The distance D2 corresponds to the distance between the centers of the second light-emitting element 60 and the second light-receiving element 61 in plan view from the Z-axis direction. The distance D3 corresponds to the distance between the centers of the third light-emitting element 70 and the second light-receiving element 61 in plan view from the Z-axis direction.

In the detecting device 3 according to the first embodiment, the distance D1 from the first light-emitting element 50 to the first light-receiving element 51 is shorter than the distance D2 from the second light-emitting element 60 to the second light-receiving element 61. The distance D1 from the first light-emitting element 50 to the first light-receiving element 51 is shorter than the distance D3 from the third light-emitting element 70 to the second light-receiving element 61. Note that the distance D2 and the distance D3 are equal.

In this manner, the detecting device 3 according to the first embodiment has a configuration in which the first light-receiving element 51 for receiving the green light LG is disposed closest to the first light-emitting element 50 emitting the green light LG. That is, the first light-receiving element 51 is provided closer to the light-emitting unit portion 11 than the second light-receiving element 61 is to the light-emitting unit portion 11.

As illustrated in FIG. 4, the first light-receiving element 51 includes a sensor 511 and a band-pass filter 512. The sensor 511 includes, for example, a photo diode (PD).

The band-pass filter 512 has characteristics of selectively passing the wavelength range of the green light LG and absorbing and cutting the red light LR and the near-infrared light LI being light in the other wavelength ranges. For example, the band-pass filter 512 is formed by alternately stacking, on the sensor 511, a plurality of low refractive index layers made of, for example, silicon oxide and high refractive index layers made of, for example, titanium oxide.

An angle limiting filter limiting the incident angle of the light incident on the sensor 511 may be provided between the sensor 511 and the band-pass filter 512.

The second light-receiving element 61 includes a sensor 611 receiving the red light LR or the near-infrared light LI. The sensor 611 includes, for example, a photodiode. The second light-receiving element 61 has a different configuration from the configuration of the first light-receiving element 51 in that the second light-receiving element 61 does not include a band-pass filter selectively passing the red light LR or the near-infrared light LI. Note that an angle limiting filter limiting the incident angle of the light incident on the sensor 611 may be provided on the sensor 611.

Here, the red light LR and the near-infrared light LI exiting from the second light-emitting element 60 may partially pass through the living body and be incident on the first light-receiving element 51. In the case of the first embodiment, the first light-receiving element 51 includes the band-pass filter 512 selectively passing the green light LG. Thus, the first light-receiving element 51 can cut the red light LR and the near-infrared light LI having a wavelength range different from that of the green light LG. Thus, the first light-receiving element 51 can efficiently receive the green light LG exiting from the light-emitting element 50.

Figure 5:
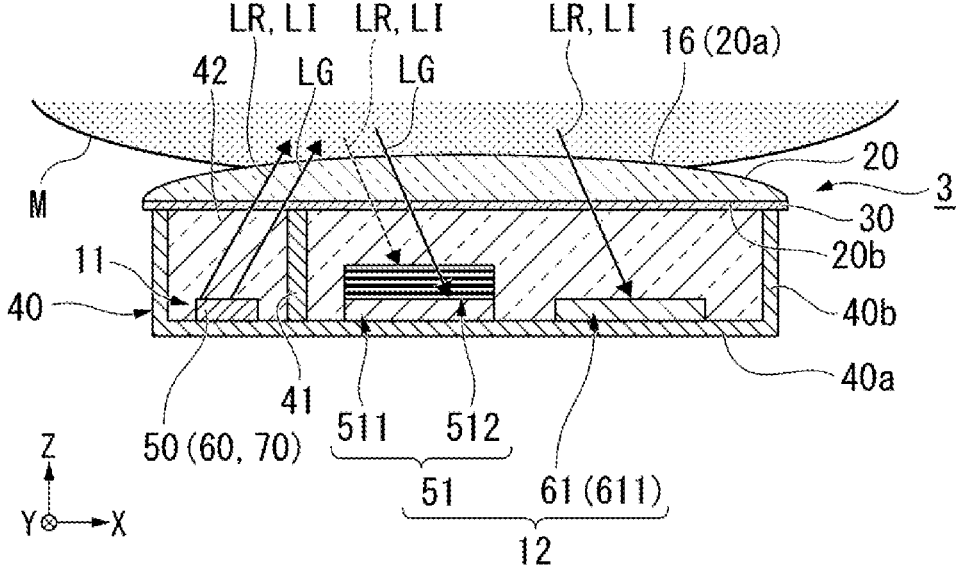
FIG. 5 is a diagram for describing an operation of the detecting device.

An operation of the detecting device 3 according to the first embodiment will be described below. FIG. 5 is a diagram for describing the operation of the detecting device 3.

For example, the green light LG exiting from the first light-emitting element 50 passes through the sealing member 42 and the intermediate member 30 in sequence and is incident on the cover member 20.

In the detecting device 3 according to the first embodiment, the intermediate member 30 having the refractive index n2 between the refractive indexes of the sealing member 42 and the cover member 30 is provided between the sealing member 42 and the cover member 30. That is, the detecting device 3 according to the first embodiment has a configuration in which no air layer is present on the optical path to a position where the light that has exited from the light-emitting unit portion 11 exits from the cover member 20.

Here, a detecting device in which the intermediate member 30 is replaced with an air layer will be considered as a comparative example. That is, the detecting device according to the comparative example has a configuration in which an air layer is present on the optical path to a position where light that has exited from the light-emitting unit portion 11 exits from the cover member 20.

In the detecting device according to the comparative example, the green light LG exiting from the light-emitting unit portion 11 is partially reflected by Fresnel reflection when incident on the air layer from the sealing member 42.

In particular, in the case of the detecting device according to the comparative example, the green light LG is incident on the air layer having a low refractive index from the sealing member 42 having a high refractive index, and thus a component incident on the air layer at an incident angle greater than a predetermined angle is totally reflected. Note that, regarding the red light LR or the near-infrared light LI exiting from the light-emitting unit portion 11, a component incident on the air layer at an incident angle greater than a predetermined angle is also totally reflected in a manner similar to the green light LG.

In this way, the light reflected by Fresnel reflection or totally reflected at the interface between the sealing member 42 and the air layer may be directly incident on the first light-receiving element 51 without passing through the living body that is the inside of the measurement site M. Hereinafter, the light toward the light-receiving elements without passing through the living body is referred to as "stray light component".

In the detecting device according to the comparative example, total reflection occurs, in addition to Fresnel reflection, at the interface between the sealing member 42 and the air layer in this manner, which increases the stray light component toward the first light-receiving element 51 and the second light-receiving element 61.

In contrast, in the case of the detecting device 3 according to the first embodiment, at the time of incidence on the intermediate member 30 from the sealing member 42, the green light LG exiting from the light-emitting unit portion 11 is incident on the intermediate member 30 having a high refractive index from the sealing member 42 having a low refractive index and thus is not totally reflected.

Furthermore, at the time of incidence on the cover member 20 from the intermediate member 30, the green light LG exiting from the light-emitting unit portion 11 is incident on the cover member 20 having a high refractive index from the intermediate member 30 having a low refractive index and thus is not totally reflected. That is, the green light LG can be efficiently incident on the measurement site M via the cover member 20 with total reflection suppressed.

In a manner similar to the green light LG, the red light LR or the near-infrared light LI exiting from the light-emitting unit portion 11 can be also efficiently incident on the measurement site M via the cover member 20 with total reflection suppressed.

Figure 6:
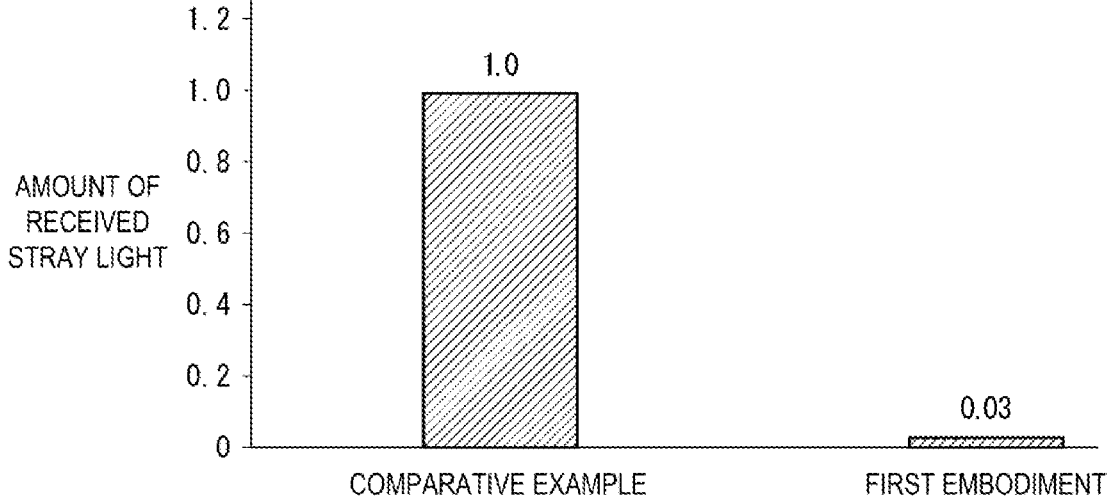
FIG. 6 is a graph of simulation results showing effectiveness of the detecting device.

The present inventors verified the effectiveness of the detecting device 3 according to the first embodiment in simulation. FIG. 6 is a graph showing simulation results. Note that, in this simulation, for example, the ratio of the light amount of the stray light component received by the first light-receiving element 51 when the green light was emitted at the same power was determined in a model corresponding to the detecting device 3 and in a model corresponding to the detecting device according to the comparative example in which the intermediate member 30 was replaced with the air layer.

As shown in FIG. 6, when the light amount of the stray light component received by the detecting device of the comparative example was 1.0, the ratio of the light amount of the stray light component received by the detecting device 3 according to the first embodiment was 0.03 (3.0%).

That is, in the detecting device according to the comparative example, it has been confirmed that the occurrence of the total reflection due to the air layer between the intermediate member 30 and the cover member 20 increases the stray light component incident on the first light-receiving element 51. On the other hand, in the detecting device 3 according to the first embodiment, it has been confirmed that the light amount of the stray light component received by the first light-receiving element 51 can be significantly reduced by providing the intermediate member 30 and eliminating the stray light component due to total reflection.

Note that the present inventors performed a similar simulation when the wavelength of emitted light was not the wavelength of green light (red light or infrared light). As a result, it has been confirmed that the light-receiving efficiency of the light-receiving element can be improved by suppressing total reflection at the interface between the sealing member 42 and the cover member 20, regardless of the wavelength range of the emitted light.

In this manner, the detecting device 3 according to the first embodiment includes the sealing member 42, the intermediate member 30, and the cover member 20, the refractive indexes of which satisfy the relationship of n1<n2<n3, and thus can suppress total reflection of light at the interface between the sealing member 42 and the cover member 20. Thus, the light exiting from the light-emitting unit portion 11 can be efficiently incident on the living body, and the light passing through the living body can be efficiently incident on the light-receiving unit portion 12.

Furthermore, the detecting device 3 according to the first embodiment can reduce stray light components incident on the first light-receiving element 51 and the second light-receiving element 61 by suppressing total reflection. Thus, the detecting device 3 according to the first embodiment can obtain a high S/N ratio by suppressing the incidence of stray light components serving as noise.

In the detecting device 3 according to the first embodiment, the cover member 20 is provided with the convex portion 20*a* as illustrated in FIG. 4, and thus a gap between the measurement site M and the cover member 20 can be reduced. This can suppress the incidence of outside light incident, as stray light components, on the light-receiving unit portion 12 from the gap between the measurement site M and the cover member 20.

In the detecting device 3 according to the first embodiment, the first light-receiving element 51 is disposed closest to the first light-emitting element 50 emitting the green light LG.

Figure 7:
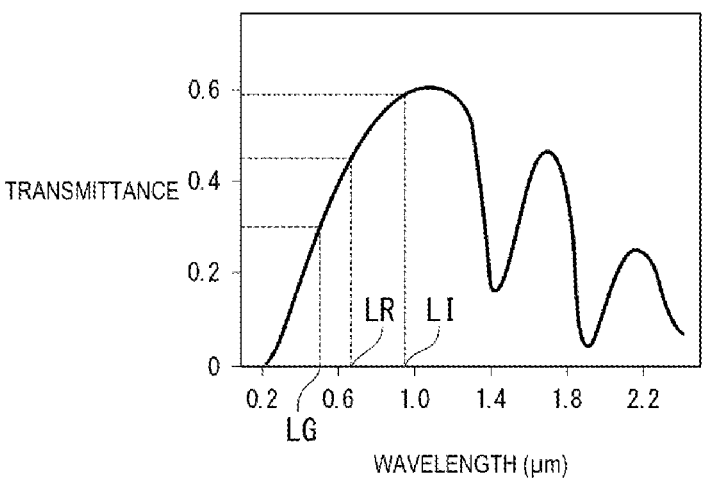
FIG. 7 is a graph showing a transmission spectrum of a skin.

FIG. 7 is a graph showing the transmission spectrum of a skin. In FIG. 7, the horizontal axis represents the wavelength of light, and the vertical axis represents the transmittance (unit: %). FIG. 7 shows the transmission spectrum when the skin has a thickness of 0.43 mm as an example.

As shown in FIG. 7, the transmittance when the wavelength range of the green light LG (e.g., 520 nm) is incident on the skin is approximately 30%, the transmittance when the wavelength range of the red light LR (e.g., 660 nm) is incident on the skin is approximately 45%, and the transmittance when the wavelength range of the near-infrared light LI (e.g., 905 nm) is incident on the skin is approximately 60%.

The graph in FIG. 7 shows that the distance that light can propagate in the living body differs depending on the wavelength of the light. That is, it can be seen from the graph in FIG. 7 that the green light LG can propagate only a shorter distance in the living body than the red light LR or the near-infrared light LI. That is, it can be said that the red light LR and the near-infrared light LI can propagate farther in the living body than the green light LG. Note that although FIG. 7 shows an example in which the skin has a thickness of 0.43 mm, it can be said that the red light LR and the near-infrared light LI can similarly propagate further in the living body than the green light LG when the skin has a different thickness.

In this manner, in the detecting device 3 according to the first embodiment, the first light-receiving element 51 and the first light-emitting element 50 are disposed close to each other, so that the green light LG exiting from the first light-emitting element 50 propagates only a short distance in the living body and is incident on the first light-receiving element 51. As illustrated in the graph in FIG. 7, the green light LG can propagate only a short distance in the living body. Thus, the green light LG from the living body can be incident on the first light-receiving element 51 at high intensity when the distance between the first light-emitting element 50 emitting the green light LG and the first light-receiving element 51 receiving the green light LG is short. Thus, the detecting device 3 according to the first embodiment can sufficiently detect, at the first light-receiving element 51, the green light LG propagating in the living body even when the light emission amount of the green light LG from the first light-emitting element 50 is suppressed.

Thus, the detecting device 3 according to the first embodiment can accurately detect the green light LG at the first light-receiving element 51 while suppressing the light emission amount of the green light LG exiting from the first light-emitting element 50 and reducing the power consumption of the light-emitting unit portion 11.

In the detecting device 3 according to the first embodiment, the distance between the second light-emitting element 60 or the third light-emitting element 70 and the second light-receiving element 61 (the distance D2 or the distance D3) is greater than the distance D1 between the first light-emitting element 50 and the first light-receiving element 51. That is, the distance that the red light LR and the near-infrared light LI propagate in the living body before being incident on the second light-receiving element 61 is greater than the distance that the green light LG propagates in the living body before being incident on the first light-receiving element 51.

As shown in FIG. 7, the green light LG can propagate only a shorter distance in the living body than the red light LR or the near-infrared light LI. Thus, if the green light LG propagates in the living body so as to be reachable to the second light-receiving element 61, the green light LG is sufficiently attenuated when passing through the living body. Therefore, the green light LG cannot be incident on the second light-receiving element 61.

On the other hand, the red light LR and the near-infrared light LI can propagate farther in the living body than the green light LG. Thus, even when the red light LR and the near-infrared light LI propagate a longer distance in the living body than the green light LG, the red light LR and the near-infrared light LI having sufficient light amounts can be incident on the second light-receiving element 61 further separated from the light-emitting unit portion 11.

In the case of the first embodiment, only the red light LR and the near-infrared light LI are incident on the second light-receiving element 61, and thus the second light-receiving element 61 does not need to be provided with a band-pass filter selectively passing the red light LR and the near-infrared light LI and cutting the green light LG. That is, the detecting device 3 according to the first embodiment can adopt a configuration in which only the first light-receiving element 51 includes the band-pass filter 512, and the second light-receiving element 61 does not include a band-pass filter. Thus, in the detecting device 3 according to the first embodiment, the omission of the band-pass filter of the second light-receiving element 61 enables cost reduction.

As described above, the detecting device 3 according to the first embodiment can achieve high detection accuracy by eliminating stray light components due to total reflection and increasing the S/N ratio of the light-receiving unit portion 12. Thus, the light-receiving unit portion 12, which has high detection accuracy, can sufficiently receive light even when the light amount is small, so that the power consumption of the light-emitting unit portion 11 can be suppressed by suppressing the light emission amount of each of the light-emitting elements 50, 60, and 70.

Therefore, the measuring apparatus 100 according to the first embodiment includes the above detecting device 3, and thus it is possible to provide a biometer that enables high accuracy detection while suppressing the power consumption.

Second Embodiment

Next, a detecting device according to a second embodiment will be described. The detecting device according to the second embodiment is different from the detecting device according to the first embodiment in a configuration of a cover member. Hereinafter, configurations and members common to those of the first embodiment will be given identical reference signs, and the reference signs will be omitted in detail description.

Figure 8:
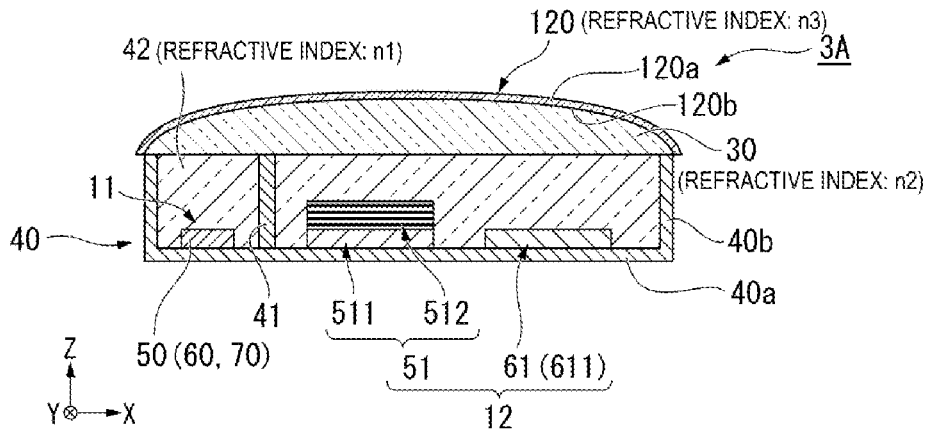
FIG. 8 is a cross-sectional view illustrating a configuration of a detecting device according to a second embodiment.

FIG. 8 is a cross-sectional view illustrating a configuration of the detecting device according to the second embodiment. FIG. 8 is a view corresponding to FIG. 4 of the first embodiment.

As illustrated in FIG. 8, a detecting device 3A according to the second embodiment includes a light-emitting unit portion 11, a light-receiving unit portion 12, a cover member 120, an intermediate member 30, a housing 40, and a sealing member 42.

The cover member 120 according to the second embodiment has a dome shape and includes a convex portion 120a and a concave portion 120b, the concave portion 120b being provided on the opposite side of the convex portion 120a and recessed toward the convex portion 120a. At least a part of the intermediate member 30 is disposed at the concave portion 120b. In the case of the second embodiment, the entire intermediate member 30 is disposed at the concave portion 120b. That is, the concave portion 120b of the cover member 120 is filled with the intermediate member 30 without gap. The cover member 120 is joined to the sealing member 42 and the housing 40 via the intermediate member 30 disposed at the concave portion 120b. The intermediate member 30 may be disposed so as to protrude from the concave portion 120b of the cover member 120.

The detecting device 3A according to the second embodiment can be assembled, for example, as follows: the concave portion 120b of the cover member 120 is filled with a liquid optical adhesive (the intermediate member 30 before curing), the housing 40 sealed by the sealing member 42 is then put on the cover member 120 from above, and the optical adhesive is cured. That is, the cover member 120 is available as a container accommodating the optical adhesive when the detecting device 3A is assembled.

In the second embodiment, the refractive indexes of the sealing member 42, the intermediate member 30, and the cover member 120 also satisfy the relationship of n1<n2<n3. That is, in the second embodiment, the detecting device 3A also has a configuration in which the intermediate member 30 having a refractive index between the refractive indexes of the sealing member 42 and the cover member 120 is interposed between the sealing member 42 and the cover member 120 located on the optical path where the light exiting from the light-emitting unit portion 11 travels.

As in the above embodiment, the detecting device 3A according to the second embodiment obtains a high S/N ratio at the light-receiving unit portion 12 by eliminating stray light components due to total reflection, which allows the green light LG, the red light LR, or the near-infrared light LI passing through the living body to be detected with higher accuracy. As a result, power consumption can be reduced.

Third Embodiment

Next, a detecting device according to a third embodiment will be described. The detecting device according to the third embodiment is different from the detecting device according to the first embodiment in a configuration of a cover member. Hereinafter, configurations and members common to those of the first embodiment will be given identical reference signs, and the reference signs will be omitted in detail description.

Figure 9:
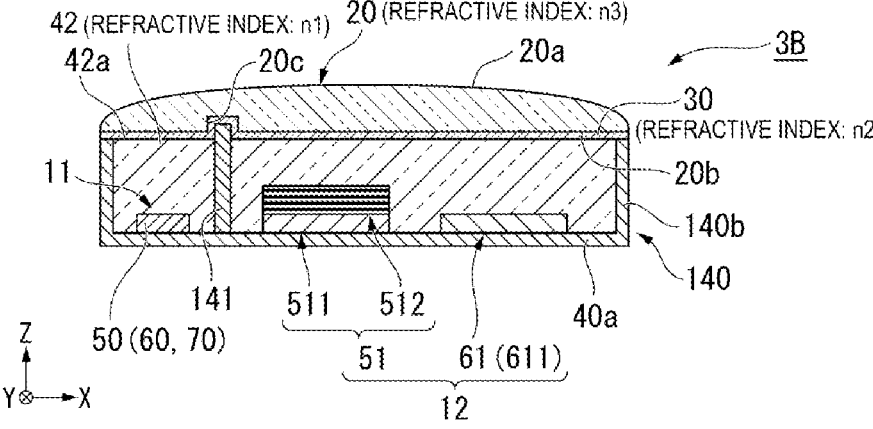
FIG. 9 is a cross-sectional view illustrating a configuration of a detecting device according to a third embodiment.

FIG. 9 is a cross-sectional view illustrating a configuration of the detecting device according to the third embodiment. FIG. 9 is a view corresponding to FIG. 4 of the first embodiment.

As illustrated in FIG. 9, a detecting device 3B according to the third embodiment includes a light-emitting unit portion 11, a light-receiving unit portion 12, a cover member 20, an intermediate member 30, a housing 140, and a sealing member 42.

The housing 140 according to the third embodiment has a box shape and includes a bottom surface portion 40a having a rectangular flat-plate shape, a wall portion 140b having a rectangular frame shape and protruding from the peripheral edge of the bottom surface portion 40a toward the +Z-side, and a wall portion 141 for light shielding.

In the third embodiment, the housing 140 includes a recessed portion 20c into which at least one of the plurality of wall portions 140b and 141 is inserted. In the case of the third embodiment, the wall portion 141 for light shielding protrudes more upward (+Z side) than the wall portion 140b. Additionally, the wall portion 141 protrudes upward (+Z side) from the upper surface 42a of the sealing member 42.

The cover member 20 according to the third embodiment is provided with a recessed portion 20c for avoiding contact with the wall portion 141 of the housing 140 at a surface 20b on the opposite side of the convex portion 20a. The wall portion 141 for light shielding is inserted into the recessed portion 20c of the cover member 20. The intermediate member 30 is disposed between the wall portion 141 inserted into the recessed portion 20c and the recessed portion 20c.

Here, the cover member 20 and the housing 140 accommodating the light-emitting unit portion 11 and the light-receiving unit portion 12 need to be accurately positioned. In a case where the wall portion 141 is fit into the recessed portion 20c, a gap is likely to be formed between the wall portion 141 and the recessed portion 20c, for example, even if the tolerances of the cover member 20 and the housing 140 are strictly controlled and parts are made with high accuracy.

In contrast, the detecting device 3B according to the third embodiment has a configuration in which the size of the recessed portion 20c is designed to be sufficiently larger than the size of the wall portion 141, and the gap formed between the recessed portion 20c and the wall portion 141 is filled with the intermediate member 30. According to the detecting device 3B of the third embodiment, a transparent adhesive material or a transparent resin is applied to the surface of the sealing member 42 and then cured with the wall portion 141 of the housing 140 inserted into the recessed portion 20c of the cover member 20, so that the configuration of FIG. 9 in which the gap between the recessed portion 20c and the wall portion 141 is filled with the intermediate member 30 can be assembled. Thus, according to the detecting device 3B of the third embodiment, even when the housing 140 has a configuration in which the wall portion 141 protrudes with respect to the other wall portion 140b, the tolerances of the parts do not need to be strictly controlled and manufacturing is facilitated. This enables cost reduction.

As in the above embodiments, the detecting device 3B according to the third embodiment obtains a high S/N ratio at the light-receiving unit portion 12 by eliminating stray light components due to total reflection, so that the green light LG, the red light LR, or the near-infrared light LI passing through the living body can be detected with higher accuracy. Furthermore, in the detecting device 3B according to the third embodiment, the wall portion 141 for light shielding is high, and thus light is difficult to be directly incident on the light-receiving unit portion 12 from the light-emitting unit portion 11. This makes it easier to suppress the incidence of stray light components on the light-receiving unit portion 12, which can further improve the detection accuracy of the light-receiving unit portion 12. Therefore, power consumption can be further reduced.

Fourth Embodiment

Next, a detecting device according to a fourth embodiment will be described. The detecting device according to the fourth embodiment is different from the detecting device according to the first embodiment in a configuration of a cover member. Hereinafter, configurations and members common to those of the first embodiment will be given identical reference signs, and the reference signs will be omitted in detail description.

Figure 10:
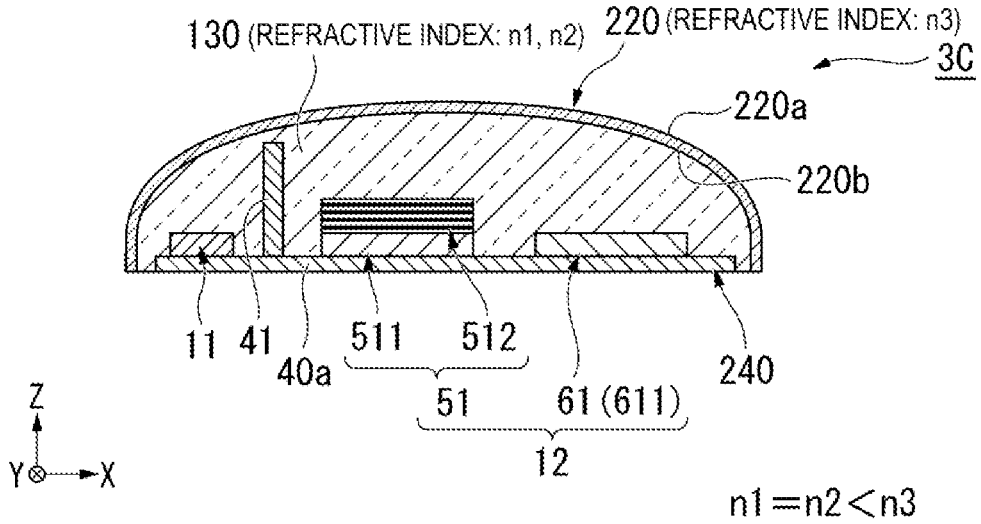
FIG. 10 is a cross-sectional view illustrating a configuration of a detecting device according to a fourth embodiment.

FIG. 10 is a cross-sectional view illustrating a configuration of the detecting device according to the fourth embodiment. FIG. 10 is a view corresponding to FIG. 4 of the first embodiment.

As illustrated in FIG. 10, a detecting device 3C according to the fourth embodiment includes a light-emitting unit portion 11, a light-receiving unit portion 12, a cover member 220, a sealing joint material 130, and a housing 240.

The cover member 220 according to the fourth embodiment has a dome shape and includes a convex portion 220*a* and a concave portion 220*b*, the concave portion 220*b* being provided on the opposite side of the convex portion 220*a* and recessed toward the convex portion 220*a*. The housing 240 according to the fourth embodiment includes a bottom surface portion 40*a* having a rectangular flat-plate shape and a wall portion 41 for light shielding.

The sealing joint material 130 is a transparent material sealing (molding to) the light-emitting unit portion 11 and the light-receiving unit portion 12. In the case of the fourth embodiment, the sealing joint material 130 is disposed at the concave portion 220*b* of the cover member 220. The cover member 220 is joined to the housing 240 via the sealing joint material 130 disposed at the concave portion 220*b*. In the case of the fourth embodiment, the sealing joint material 130 serves as a sealing member and a light transmissive member. That is, the sealing member and the light transmissive member are composed of a single material. In the fourth embodiment, of the sealing member, the light transmissive member, and the cover member, the sealing member and the light transmissive member, which are two members in contact with each other, are composed of a single material.

The detecting device 3C according to the fourth embodiment can be assembled, for example, as follows: the concave portion 220*b* of the cover member 220 is filled with a liquid optical adhesive (the sealing joint material 130 before curing), the housing 240 holding the light-emitting unit portion 11 and the light-receiving unit portion 12 is put on the cover member 220 from above, and the optical adhesive is cured. That is, the cover member 220 is available as a container accommodating the optical adhesive when the detecting device 3C is assembled.

In the case of the fourth embodiment, the sealing joint material 130 serves as the sealing member and the light transmissive member, and thus the refractive indexes of the sealing member, the light transmissive member, and the cover member 220 satisfy the relationship of n1=n2<n3. That is, in the fourth embodiment, the detecting device 3C also has a configuration in which an interface where a large refractive index changes to a small refractive index, i.e., an interface that causes total reflection, is not present on the optical path where the light exiting from the light-emitting unit portion 11 travels.

In the fourth embodiment, the sealing joint material 130 serving as the sealing member and the light transmissive member is composed of a single material and thus has no interface therein, so that the light exiting from the light-emitting unit portion 11 reaches the cover member 220 without being reflected in the sealing joint material 130. The refractive index of the sealing joint material 130 is smaller than the refractive index of the cover member 220, and thus the light exiting from the light-emitting unit portion 11 is not totally reflected at the interface between the sealing joint material 130 and the cover member 220.

As in the above embodiments, the detecting device 3C according to the fourth embodiment obtains a high S/N ratio at the light-receiving unit portion 12 by eliminating stray light components due to total reflection, so that the green light LG, the red light LR, or the near-infrared light LI passing through the living body can be detected with higher accuracy. Further, in the detecting device 3C according to the fourth embodiment, the sealing joint material 130 composed of a single material is used as the sealing member and the light transmissive member, and thus the interface between the sealing member and the light transmissive member is eliminated. This can further reduce the light loss due to Fresnel reflection.

The present disclosure has been described based on the above embodiments. However, the present disclosure is not limited to the above embodiments and can be embodied in various aspects without departing from the gist of the disclosure.

For example, a human has been described as an example of the living body in the above embodiments, but the present disclosure is also applicable to measurement of biological information (e.g., pulse) of other animals.

In the detecting device 3 according to the first embodiment, the case where the cover member 20 is attached to the housing 40 has been described as an example, but the cover member 20 may be supported by the main body 1 of the measuring apparatus 100. The cover member 20 may be constituted by a part of the rear lid of the main body 1 of the measuring apparatus 100.

In this case, the intermediate member 30 does not need to have an adhesive function and is made of, for example, a viscous material having a predetermined refractive index. In this case, the detecting device and the measuring apparatus have been assembled by disposing the viscous material on the housing 40 incorporated at a predetermined position in the main body 1 and then attaching the cover member 20 to the main body 1.

In addition, in the measuring apparatus 100 according to the first embodiment, the plano-convex cover member 20 having one surface configured as a curved surface and another surface configured as a flat surface has been described as an example, but the shape of the cover member is not limited to a plano-convex shape. For example, a plate-shaped cover member having both surfaces configured as flat surfaces may be used.

Further, in the measuring apparatus 100 according to the first embodiment, the case where the detecting device 3 is provided in the main body 1 has been described as an example, but the installation position of the detecting device 3 is not limited thereto, and the detecting device 3 may be embedded, for example, on the back side of the belt.

The configuration of a wristwatch type has been described as an example of the configuration of the measuring apparatus 100 according to the first embodiment. However, the present disclosure can be applied to, for example, a configuration in which a necklace-type measuring apparatus is mounted at the neck of the subject, a configuration in which a seal-type measuring apparatus is mounted, being pasted on the body of the subject, and a configuration in which a head-mounted display type measuring apparatus is mounted at the head of the subject.

Further, in the detecting device 3 according to the first embodiment, the case where the light-emitting elements 50, 60, and 70 emit light in a time-division manner has been described as an example. However, the first light-receiving element 51 corresponding to the green light LG from the first light-emitting element 50 is individually provided, and thus the first light-emitting element 50 may emit light at all times, not in a time-division manner. Note that the first light-emitting element 50 may similarly emit light at all times, not in a time-division manner, in the second to fourth embodiments.

In the detecting device 3C according to the fourth embodiment, the case where the sealing joint material 130 serves as the sealing member and the light transmissive member has been described as an example, but the sealing member 130 may serve as all of the sealing member, the light transmissive member, and the cover member. In this case, because the sealing joint member 130 serves as all of the sealing member, the light transmissive member, and the cover member, the refractive indexes of the sealing member, the light transmissive member, and the cover member satisfy the relationship of $n1=n2=n3$. In other words, there is no difference in the refractive index on the optical path where the light exiting from the light-emitting unit portion 11 travels, and thus the light loss due to Fresnel reflection, in addition to total reflection, can be reduced. Thus, power consumption can be further reduced by increasing the light use efficiency of the light-emitting unit portion 11.

In this manner, the configuration in which the sealing joint material serves as all of the sealing member, the light transmissive member, and the cover member can be assembled, for example, as follows: a metal mold having the same shape as the cover member 220 is filled with a liquid optical adhesive (the sealing joint material before curing), the housing 240 holding the light-emitting unit portion 11 and the light-receiving unit portion 12 is then put on the metal mold from above, the liquid optical adhesive is cured, and the metal mold is removed.

Additionally, in the detecting device 3A according to the second embodiment, the intermediate member 30 may serve as both of the light transmissive member and the cover member. That is, of the sealing member, the light transmissive member, and the cover member, the light transmissive member and the cover member, which are two members in contact with each other, may be composed of a single material. In this case, the refractive indexes of the sealing member, the light transmissive member, and the cover member satisfy the relationship of $n1<n2=n3$.

The configuration in which the intermediate member 30 serves as the light transmissive member and the cover member can be assembled, for example, as follows: a metal mold having the same shape as the cover member 120 illustrated in FIG. 8 is filled with a liquid optical adhesive (the intermediate member before curing), the housing 40 sealed by the sealing member 42 is then put on the metal mold from above, the liquid optical adhesive is cured, and the metal mold is removed.

The detecting device according to an aspect of the present disclosure may have the following configuration.

The detecting device according to an aspect of the present disclosure includes a light-emitting portion emitting light, a light-receiving portion receiving the light emitted from the light-emitting portion and exiting from a living body, a case accommodating the light-emitting portion and the light-receiving portion, a sealing member sealing the light-emitting portion and the light-receiving portion in the case, a cover member covering the case sealed by the sealing member, and a light transmissive member interposed between the sealing member and the cover member and made of light transmissive resin, wherein $n1 \le n2 \le n3$, where $n1$ is a refractive index of the sealing member, $n2$ is a refractive index of the light transmissive member, and $n3$ is a refractive index of the cover member.

The detecting device according to an aspect of the present disclosure may have a configuration in which the cover member includes a convex portion including a curved surface protruding toward the living body.

The detecting device according to an aspect of the present disclosure may have a configuration in which the cover member further includes a concave portion, the concave portion being provided on an opposite side of the convex portion and recessed toward the convex portion, and at least a part of the light transmissive member is disposed at the concave portion.

The detecting device according to an aspect of the present disclosure may have a configuration in which the case includes a wall plate protruding from the sealing member toward the cover member, the cover member includes a recessed portion, the wall plate being inserted into the recessed portion, and the light transmissive member is disposed between the recessed portion and the wall plate.

The detecting device according to an aspect of the present disclosure may have a configuration in which the sealing member, the light transmissive member, and the cover member are composed of a single material.

The detecting device according to an aspect of the present disclosure may have a configuration in which, of the sealing member, the light transmissive member, and the cover member, two members in contact with each other are composed of a single material.

The detecting device according to an aspect of the present disclosure may have a configuration in which the light-emitting portion includes a first light-emitting element emitting first light having a green wavelength range and a second light-emitting element emitting second light having a wavelength range longer than the green wavelength range, the light-receiving portion includes a first light-receiving element receiving the first light emitted from the first light-emitting element and exiting from a living body and a second light-receiving element receiving the second light emitted from the second light-emitting element and exiting from the living body, when a direction of arrangement of the first light-emitting element and the second light-emitting element is defined as a first direction and a direction intersecting the first direction is defined as a second direction, the first light-receiving element is provided closer to the light-emitting portion in the second direction than the second light-receiving element is to the light-emitting portion in the second direction.

The detecting device according to an aspect of the present disclosure may have a configuration in which the light-emitting portion further includes a third light-emitting element emitting third light having a wavelength range longer than the wavelength range of the second light, and the third light emitted from the third light-emitting element and exiting from the living body is received by the second light-receiving element.

The detecting device according to an aspect of the present disclosure may have the following configuration.

The detecting device according to an aspect of the present disclosure includes a light-emitting portion emitting light to a living body, a light-receiving portion receiving the light from the living body, a holding member holding the light-emitting portion and the light-receiving portion, a wall portion for light shielding disposed, at the holding member, between the light-emitting portion and the light-receiving portion, a sealing member sealing the light-emitting portion and the light-receiving portion, a cover member covering the holding member sealed by the sealing member, and a light transmissive member interposed between the sealing member and the cover member, wherein the wall portion is formed to divide the sealing member into an accommodation space for the light-emitting portion and an accommodation space for the light-receiving portion and to reach the light transmissive member from a bottom surface portion of the holding member, and a refractive index value of the light transmissive member is equal to or less than a refractive index value of the cover member.

The measuring apparatus according to an aspect of the present disclosure may have the following configuration.

The measuring apparatus according to an aspect of the present disclosure includes the detecting device according to the above aspect and an information analysis portion determining biological information from a detection signal indicating a detection result from the detecting device.

What is claimed is:

1. A detecting device comprising:

a light-emitting diode configured to emit a light toward a living body;

a photodiode configured to receive the light emitted from the light-emitting diode and exiting from the living body;

a housing that holds the light-emitting diode and the photodiode;

a transparent material that covers the light-emitting diode and the photodiode;

a cover that covers the housing and the transparent material; and a light transmissive layer that is interposed between the transparent material and the cover, wherein $n1 \leq n2 \leq n3$ where n1 is a refractive index of the transparent material, n2 is a refractive index of the light transmissive layer, and n3 is a refractive index of the cover, the housing includes a wall protruding through the transparent material toward the cover, the cover includes a recessed portion, the wall is inserted into the recessed portion, and the light transmissive layer is disposed between the wall and the recessed portion.

2. The detecting device according to claim 1, wherein the cover has a convex portion protruding toward the living body.

3. A measuring apparatus comprising:

the detecting device according to claim 1; and an information analysis portion configured to determine biological information from a detection signal indicating a detection result from the detecting device.

* * * * *